(12) United States Patent
Brown (10) Patent No.: US 8,222,467 B2
(45) Date of Patent: Jul. 17, 2012

(54) PRODUCTION OF HIGH PURITY CUMENE FROM NON-EXTRACTED FEED AND HYDROCARBON COMPOSITION USEFUL THEREIN

(75) Inventor: Stephen Harold Brown, Bernardsville, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 232 days.

(21) Appl. No.: 12/699,676

(22) Filed: Feb. 3, 2010

(65) Prior Publication Data

US 2010/0137661 A1    Jun. 3, 2010

Related U.S. Application Data

(63) Continuation-in-part of application No. 11/705,323, filed on Feb. 12, 2007, now Pat. No. 7,683,228.

(51) Int. Cl.
 *C07C 15/04* (2006.01)
 *C10M 105/02* (2006.01)
(52) U.S. Cl. ............... 585/24; 585/16; 585/20; 508/110
(58) Field of Classification Search .............. 585/16, 585/20, 24; 508/110
See application file for complete search history.

(56) References Cited

U.S. PATENT DOCUMENTS

| | | | |
|---|---|---|---|
| 1,491,998 A | 4/1924 | Midgley, Jr. | |
| 4,291,185 A | 9/1981 | Kaeding | |
| 5,149,894 A | 9/1992 | Holtermann et al. | |
| 6,177,600 B1 | 1/2001 | Netzer | |
| 6,313,362 B1 | 11/2001 | Green et al. | |
| 6,339,179 B1 | 1/2002 | Schulz et al. | |
| 6,355,851 B1 | 3/2002 | Wu et al. | |
| 6,491,809 B1 * | 12/2002 | Briot et al. | 208/18 |
| 6,500,996 B1 | 12/2002 | Brown et al. | |
| 6,765,120 B2 | 7/2004 | Weber et al. | |
| 6,781,023 B2 | 8/2004 | Brown et al. | |
| 6,884,916 B1 | 4/2005 | Brown et al. | |
| 7,244,522 B2 * | 7/2007 | Gunsel et al. | 428/835.6 |
| 7,683,228 B2 * | 3/2010 | Brown | 585/447 |
| 2001/0045376 A1 | 11/2001 | Brown et al. | |
| 2003/0092952 A1 | 5/2003 | Netzer | |
| 2006/0247479 A1 | 11/2006 | Barchha et al. | |
| 2010/0210886 A1 * | 8/2010 | Brown et al. | 585/323 |

FOREIGN PATENT DOCUMENTS

| | | |
|---|---|---|
| GB | 606811 | 8/1948 |
| WO | WO 2006/032400 | 3/2006 |
| WO | WO 2006/060158 | 6/2006 |

* cited by examiner

*Primary Examiner* — Ellen McAvoy
(74) *Attorney, Agent, or Firm* — Darryl M. Tyus (57) ABSTRACT

A non-extracted hydrocarbon composition feed is substantially free of both $C_4-$ hydrocarbons and the $C_7+$ aromatic hydrocarbons and contains benzene and benzene coboilers as well as sulfur, nitrogen, olefins and dienes.

8 Claims, 4 Drawing Sheets

PRODUCTION OF HIGH PURITY CUMENE FROM NON-EXTRACTED FEED AND HYDROCARBON COMPOSITION USEFUL THEREIN

CROSS-REFERENCE TO RELATED APPLICATIONS

This application claims priority as a continuation-in-part of U.S. Ser. No. 11/705,323, filed Feb. 12, 2007, now U.S. Pat. No. 7,683,228, the entire contents of which are hereby incorporated by reference herein.

FIELD OF THE INVENTION

This disclosure relates to a non-extracted hydrocarbon composition and a process for producing high purity cumene by the propylation of benzene present in the non-extracted hydrocarbon composition feed.

BACKGROUND OF THE INVENTION

Cumene (isopropylbenzene) is a key raw material in the production of phenol and acetone and is produced primarily by the propylation reaction of propylene, $C_3H_6$, and benzene, $C_6H_6$, in a catalytic environment. Cumene is then converted to phenol and acetone by peroxidation. When sold as a commodity product, the product will usually contain at least 99.70 weight percent of cumene based on the weight of the product.

A source of benzene is reformate, which is prepared by contacting a mixture of petroleum naphtha and hydrogen with a reforming catalyst containing a support, e.g., halogen-treated alumina or non-acidic zeolite L, and a hydrogenation/dehydrogenation metal, e.g., Group 8, 9, or 10 metal such as platinum. That process typically produces a reformate that includes $C_5-$ hydrocarbons, $C_6-C_8$ aromatic hydrocarbons, e.g., benzene, $C_9+$ hydrocarbons, $C_6+$ paraffins, and cycloparaffins (naphthenes).

Another source of benzene is the cracking of hydrocarbons such as by steam cracking or catalytic cracking. That process typically produces an effluent that includes $C_6-C_8$ aromatic hydrocarbons, e.g., benzene, $C_6+$ paraffins, and naphthenes.

Still another source for producing aromatics is the dehydrocyclo-oligomerization of $C_2-C_5$ aliphatic hydrocarbons. That process typically produces a product effluent that includes $C_6-C_8$ aromatic hydrocarbons, e.g., benzene, $C_6+$ paraffins, naphthenes and $C_5$ aliphatic hydrocarbons.

Benzene can be separated from other reformate hydrocarbons, e.g., $C_7+$ aromatics, by distillation. However, the benzene obtained by distillation will usually contain $C_6$ and $C_7$ non-aromatic hydrocarbon impurities that are difficult to separate from benzene by distillation because they have boiling points close to the boiling point of benzene, i.e., their boiling point is within 10° C. of benzene (boiling point of 80.1° C.) at a pressure of about 101.3 kPa-a (absolute). This feed may also contain $C_5$ paraffins and naphthenes, such as n-pentane and cyclopentane. These impurities, which are hereinafter sometimes referred to as "benzene coboilers", may be present in the distillate product in an amount up to 75 percent by weight based on the weight of the product. Examples of benzene coboilers include cyclohexane, methylcyclopentane, 2-methylhexane, 3-methylhexane, 2,3-dimethylpentane, 2,4-dimethylpentane, and dimethylcyclopentane.

Because of the presence of benzene coboilers, the feed usually undergoes an additional step, i.e., extraction such as liquid extraction or extractive distillation, to remove benzene coboilers from the benzene product before the benzene is propylated to form cumene. Generally, benzene used in the propylation of benzene to produce high purity cumene has a purity of about at least 99.985 weight percent by weight based on the weight of benzene present in the benzene distillate. However, the extraction step is expensive and time consuming, which results in increased costs in manufacture of high purity cumene. It would be highly advantageous to use lower cost refinery streams rich in benzene, for example, aromatizer product streams which have not undergone extraction to produce high purity cumene.

In addition, processes for producing cumene by the propylation of benzene usually result in the formation of polypropylbenzenes which are processed by transalkylation with benzene to form cumene. A problem associated with the transalkylation of polypropylbenzenes is that several impurities, e.g., ethylbenzene, are usually formed as by-products. Formation of by-product ethylbenzene is industrially disadvantageous because its boiling point is relatively close to that of cumene. As a result, the separation of ethylbenzene from cumene to obtain high purity cumene requires the use of a special distillation column which results in increased costs in manufacture of high purity cumene.

By the present disclosure, a process is provided for the propylation of benzene to produce high purity cumene that uses a hydrocarbon composition feed containing benzene that has not undergone extraction. In addition, the process of the present disclosure does not require the transalkylation of the polypropylbenzenes formed during the propylation of benzene.

SUMMARY OF THE INVENTION

The present disclosure is directed to a benzene-containing hydrocarbon composition that has not undergone extraction and finds particular application in the production of high purity cumene by the propylation of benzene contained in the hydrocarbon composition. The hydrocarbon composition is substantially free of $C_4-$ hydrocarbons and $C_7+$ aromatic hydrocarbons and contains: (i) benzene; (ii) from about 1 to about 75 percent by weight based on the weight of the hydrocarbon composition, of at least one $C_6+$ non-aromatic hydrocarbon having a boiling point within 10° C. at a pressure of about 101.3 kPa-a of the boiling point of benzene; (iii) up to 5 wppm of sulfur; (iv) up to 1 wppm of nitrogen; and, (v) up to 2500 wppm of olefins and dienes.

DETAILED DESCRIPTION OF THE INVENTION

All patents, patent applications, test procedures, priority documents, articles, publications, manuals, and other documents cited herein are fully incorporated by reference to the extent such disclosure is not inconsistent with the present disclosure and for all jurisdictions in which such incorporation is permitted.

When numerical lower limits and numerical upper limits are listed herein, ranges from any lower limit to any upper limit are contemplated.

As used in this specification, the term "framework type" is used in the sense described in the "Atlas of Zeolite Framework Types," 2001.

As used herein, the numbering scheme for the Periodic Table Groups is used as in Chemical and Engineering News, 63(5), 27 (1985).

The term "aromatization", as used herein, shall mean the production of aromatics comprising benzene, toluene, or mixtures thereof by the conversion of non-aromatic hydrocarbons to aromatic hydrocarbons comprising benzene, toluene, or mixtures thereof. The term "aromatization", as used herein, shall also include the production of aromatics comprising benzene, toluene, or mixtures thereof by the cracking of heavy aromatic hydrocarbons to produce the aromatic hydrocarbons comprising benzene, toluene, or mixtures. Examples of aromatization processes include catalytic reforming of naphtha, dehydrocyclo-oligomerization of $C_2$-$C_5$ aliphatic hydrocarbons, steam cracking of hydrocarbons to produce aromatic hydrocarbons comprising benzene, toluene, or mixtures thereof, and the catalytic cracking of hydrocarbons to produce aromatic hydrocarbons comprising benzene, toluene, or mixtures thereof.

The term "reformate", as used herein, shall mean the product produced by "aromatization".

As used herein, an "alkylatable aromatic compound" is a compound that may receive an alkyl group and an "alkylating agent" is a compound which may donate an alkyl group to an alkylatable aromatic compound. One example of the alkylatable aromatic compounds is benzene. Examples of the alkylating agent are ethylene, propylene, polyalkylated aromatic compound(s), e.g., di-ethylbenzene, tri-ethylbenzene, di-isopropylbenzene, and tri-isopropylbenzene The term "wppm" as used herein is defined as parts per million by weight.

The term "at least partially in liquid phase" as used herein is understood as a mixture having at least 1 wt. % liquid phase, optionally at least 5 wt. % liquid phase at a given temperature, pressure, and composition.

The term "substantially in liquid phase" as used herein is understood as a mixture having at least 95 wt. % liquid phase, optionally at least 99 wt. % liquid phase at a given temperature, pressure, and composition.

The term "$C_n$" hydrocarbon wherein n is an positive integer, e.g., 1, 2, 3, 4, 5, 6, 7, 8, 9, 10, 11, 12, as used herein means a hydrocarbon having n number of carbon atom(s) per molecular. For example, $C_n$ aromatics means an aromatic hydrocarbon having n number of carbon atom(s) per molecular; $C_n$ paraffin means a paraffin hydrocarbon having n number of carbon atom(s) per molecular; $C_n$ olefin means an olefin hydrocarbon having n number of carbon atom(s) per molecular. The term "$C_n+$" hydrocarbon wherein n is an positive integer, e.g., 1, 2, 3, 4, 5, 6, 7, 8, 9, 10, 11, 12, as used herein means a hydrocarbon having at least n number of carbon atom(s) per molecular. The term "$C_n-$" hydrocarbon wherein n is an positive integer, e.g., 1, 2, 3, 4, 5, 6, 7, 8, 9, 10, 11, 12, as used herein means a hydrocarbon having no more than n number of carbon atom(s) per molecular.

The term "aromatic" as used herein is to be understood in accordance with its art-recognized scope which includes alkyl substituted and unsubstituted mono- and polynuclear compounds. Compounds of an aromatic character, which possess a heteroatom, are also useful provided sufficient activity can be achieved if they act as catalyst poisons under the reaction conditions selected.

The term "at least partially in liquid phase" as used herein is understood as a mixture having at least 1 wt. % liquid phase, optionally at least 5 wt. % liquid phase at a given temperature, pressure, and composition.

The term "MCM-22 family material" (or "material of the MCM-22 family" or "molecular sieve of the MCM-22 family"), as used herein, includes:

(i) molecular sieves made from a common first degree crystalline building block "unit cell having the MWW framework topology". A unit cell is a spatial arrangement of atoms which is tiled in three-dimensional space to describe the crystal as described in the "Atlas of Zeolite Framework Types", Fifth edition, 2001, the entire content of which is incorporated as reference;

(ii) molecular sieves made from a common second degree building block, a 2-dimensional tiling of such MWW framework type unit cells, forming a "monolayer of one unit cell thickness", preferably one c-unit cell thickness;

(iii) molecular sieves made from common second degree building blocks, "layers of one or more than one unit cell thickness", wherein the layer of more than one unit cell thickness is made from stacking, packing, or binding at least two monolayers of one unit cell thick of unit cells having the MWW framework topology. The stacking of such second degree building blocks can be in a regular fashion, an irregular fashion, a random fashion, and any combination thereof; or (iv) molecular sieves made by any regular or random 2-dimensional or 3-dimensional combination of unit cells having the MWW framework topology.

The MCM-22 family materials are characterized by having an X-ray diffraction pattern including d-spacing maxima at 12.4±0.25, 3.57±0.07 and 3.42±0.07 Angstroms (either calcined or as-synthesized). The MCM-22 family materials may also be characterized by having an X-ray diffraction pattern including d-spacing maxima at 12.4±0.25, 6.9±0.15, 3.57±0.07 and 3.42±0.07 Angstroms (either calcined or as-synthesized). The X-ray diffraction data used to characterize the molecular sieve are obtained by standard techniques using the K-alpha doublet of copper as the incident radiation and a diffractometer equipped with a scintillation counter and associated computer as the collection system. Materials belong to the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), ITQ-30 (described in International Patent Publication No. WO2005118476), MCM-36 (described in U.S. Pat. No. 5,250,277), MCM-49 (described in U.S. Pat. No. 5,236,575), MCM-56 (described in U.S. Pat. No. 5,362,697), and UZM-8 (described in U.S. Pat. No. 6,756,030). The entire contents of the patents are incorporated herein by reference.

It is to be appreciated the MCM-22 family molecular sieves described above are distinguished from conventional large pore zeolite alkylation catalysts, such as mordenite, in that the MCM-22 family materials have 12-ring surface pockets which do not communicate with the 10-ring internal pore system of the molecular sieve.

The zeolitic materials designated by the IZA-SC as being of the MWW topology are multi-layered materials which have two pore systems arising from the presence of both 10 and 12 membered rings. The Atlas of Zeolite Framework Types classes five differently named materials as having this same topology: MCM-22, ERB-1, ITQ-1, PSH-3, and SSZ-25.

The MCM-22 family molecular sieves have been found to be useful in a variety of hydrocarbon conversion processes. Examples of MCM-22 family molecular sieve are MCM-22, MCM-49, MCM-56, ITQ-1, PSH-3, SSZ-25, and ERB-1. Such molecular sieves are useful for alkylation of aromatic compounds. For example, U.S. Pat. No. 6,936,744 discloses a process for producing a monoalkylated aromatic compound, particularly cumene, comprising the step of contacting a polyalkylated aromatic compound with an alkylatable aromatic compound under at least partial liquid phase conditions and in the presence of a transalkylation catalyst to produce the monoalkylated aromatic compound, wherein the transalkylation catalyst comprises a mixture of at least two different crystalline molecular sieves, wherein each of the molecular sieves is selected from zeolite beta, zeolite Y, mordenite and a material having an X-ray diffraction pattern including d-spacing maxima at 12.4±0.25, 6.9±0.15, 3.57±0.07 and 3.42±0.07 Angstroms.

Figure 1:
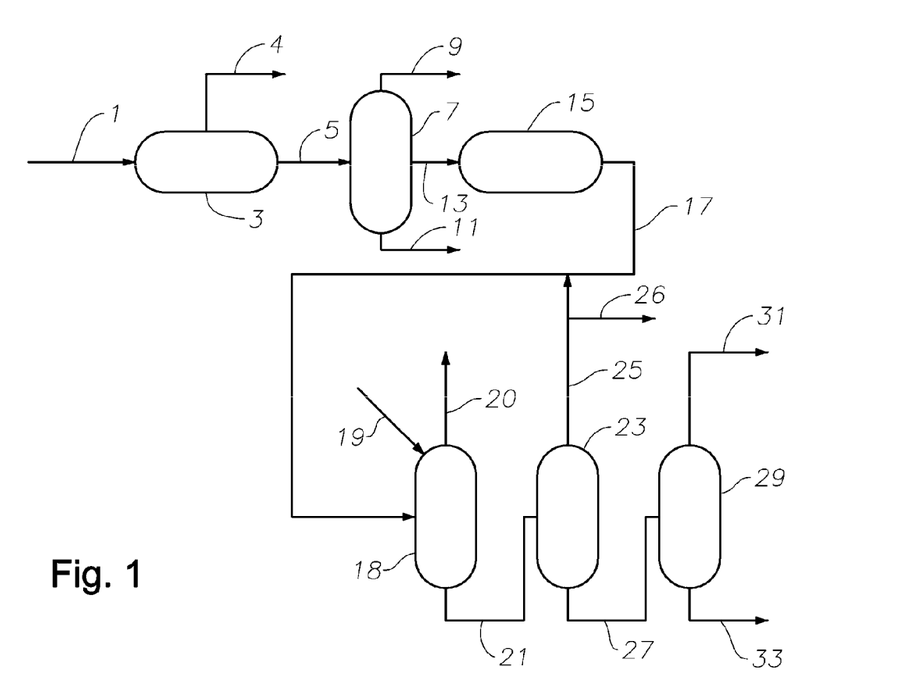
FIG. 1 is a simplified process flow diagram, illustrating an embodiment of the disclosure.

An embodiment of the present disclosure is depicted in FIG. 1. Referring to FIG. 1, naphtha is introduced via line 1 into reactor zone 3 where the naphtha is reformed or steam cracked into aromatic products including benzene. Although only one reactor zone is shown, there can be more than one reactor zone. In reactor zone 3, $C_4-$ hydrocarbons are removed from the reformate via line 4 and the remaining reformate is withdrawn from reactor zone 3 via line 5 and introduced into column 7 where the feed is fractionated to form a light reformate fraction, a heavy reformate fraction, and a benzene/benzene coboiler fraction. The light reformate fraction is withdrawn from column 7 through line 9, the heavy reformate fraction is withdrawn from column 7 through line 11, and the benzene/benzene coboiler fraction is withdrawn from column 7 through line 13 and introduced into zone 15. In zone 15, catalyst poisons, e.g., sulfur, nitrogen, olefins, dienes, or combinations thereof are at least partially removed from the benzene/benzene coboiler fraction. The resulting fraction is withdrawn from zone 15 via line 17 and introduced into propylation zone 18. In propylation zone 18, propylene is introduced via line 19 and benzene is reacted with the propylene to form cumene. Low molecular weight molecules, such as propane and propylene, are withdrawn from propylation zone 18 via line 20. The cumene-containing product is withdrawn from propylation zone 18 via line 21 and introduced into column 23. In column 23, the cumene-containing product is fractionated to form a $C_8-$ fraction and a $C_9+$ fraction comprised of cumene and polypropylbenzenes. The $C_8-$ fraction is withdrawn from column 23 via line 25 and either removed from the unit via line 26 or recycled via line 17 to propylation zone 18. The $C_9+$ fraction is withdrawn from column 23 via line 27 and introduced into column 29. In Column 29, the $C_9+$ fraction is fractionated to form a high purity cumene product fraction and a $C_{10}+$ fraction comprised of polypropylbenzenes and $C_{16}+$ hydrocarbons. The $C_{10}+$ fraction is withdrawn from column 29 via line 33. Recovered polypropylbenzenes have a high octane rating and are available for upgrading the value of mogas pool (can be blended into gasoline to increase its octane). The high purity cumene product fraction is withdrawn from column 29 via line 31 and recovered without need of further purification. The cumene product will usually have a purity that exceeds 99.50 percent by weight based on the total weight of the product.

Figure 2:
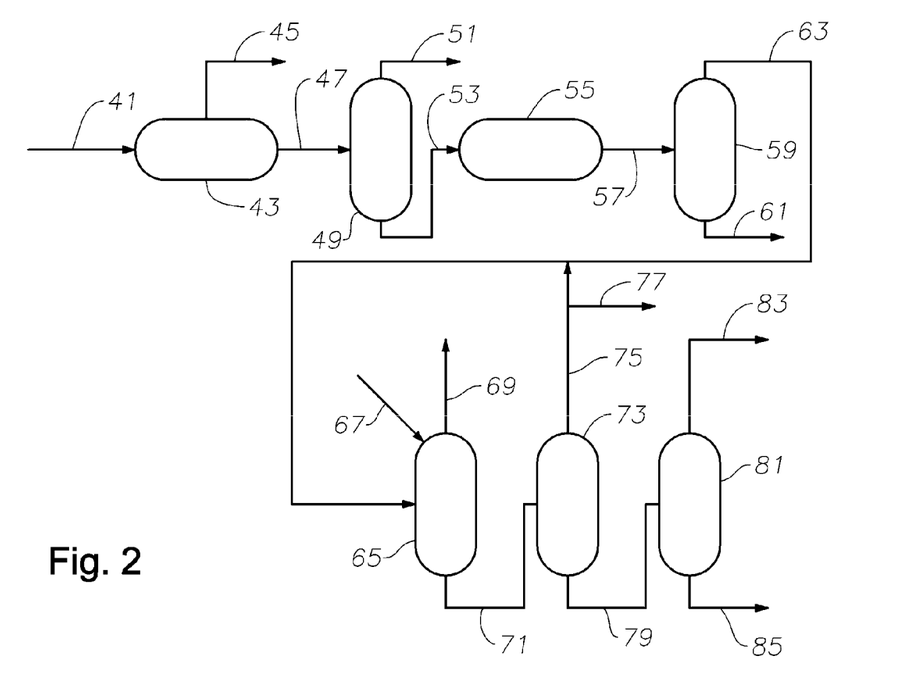
FIG. 2 is a simplified process flow diagram, illustrating another embodiment of the disclosure.

Another embodiment of the present disclosure is depicted in FIG. 2. Referring to FIG. 2, naphtha is introduced via line 41 into reactor zone 43 where the naphtha is reformed into aromatic products including benzene. Although only one reactor zone is shown, there can be more than one reactor zone. In reactor zone 43, $C_4-$ hydrocarbons are removed from the reformate via line 45 and the remaining reformate is withdrawn from reactor zone 43 via line 47 and introduced into column 49 where the feed is fractionated to form a light reformate fraction and a heavy reformate fraction. The light reformate fraction is withdrawn from column 49 through line 51 and the heavy reformate fraction containing benzene and benzene coboilers is withdrawn from column 49 through line 53, and introduced into zone 55. In zone 55, olefins, dienes, or combinations thereof are removed from the heavy reformate fraction. The resulting fraction is withdrawn from zone 55 via line 57 and introduced into column 59 where the feed is fractionated to form a benzene/benzene coboiler fraction and a $C_7+$ aromatic fraction. The $C_7+$ aromatic fraction is removed from column 59 fraction via line 61. The benzene/benzene coboiler fraction is withdrawn from column 59 via line 63 and introduced into propylation zone 65. Propylene is introduced into propylation zone 65 via line 67 and benzene is reacted with the propylene to form cumene. Low molecular weight molecules, such as propylene and propane, are withdrawn from propylation zone 65 via line 69. The cumene-containing product is withdrawn from propylation zone 65 via line 71 and introduced into column 73. In column 73, the cumene-containing product is fractionated to form a $C_8-$ fraction and a $C_9+$ fraction comprised of cumene and polypropylbenzenes. The $C_8-$ fraction is withdrawn from column 73 via line 75 and either removed from the unit via line 77 or recycled via line 63 to propylation zone 65. The $C_9+$ fraction is withdrawn from column 73 via line 79 and introduced into column 81. In Column 81, the $C_9+$ fraction is fractionated and forms a high purity cumene product fraction and a $C_{10}+$ fraction comprised of polypropylbenzenes. The $C_{10}+$ fraction is withdrawn from column 81 via line 85. Recovered polypropylbenzenes have a high octane rating and are available for upgrading the value of mogas pool (can be blended into gasoline to increase its octane). The high purity cumene product fraction is withdrawn from column 81 via line 83 and recovered without need of further purification. The cumene product will usually have a purity that exceeds 99.50 percent by weight based on the total weight of the product.

Figure 3:
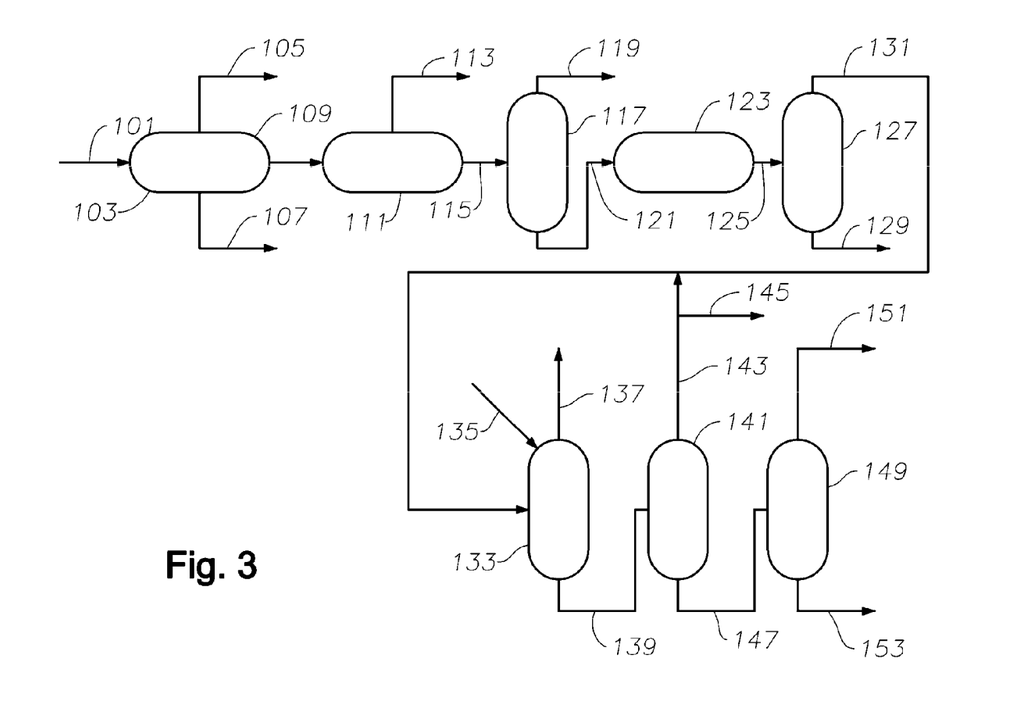
FIG. 3 is a simplified process flow diagram, illustrating a further embodiment of the disclosure.

A further embodiment of the present disclosure is depicted in FIG. 3. Referring to FIG. 3, naphtha having sufficient temperature is introduced via line 101 into reactor zone 103 where the naphtha undergoes steam cracking resulting in a product containing aromatics including benzene. Although only one reactor zone is shown, there can be more than one reactor zone. In reactor zone 103, $C_4-$ hydrocarbons are removed via line 105 and a heavy fraction is removed via line 107. A fraction containing benzene and benzene coboilers is withdrawn from reactor zone 103 via line 109 and introduced into zone 111 where the fraction is hydroprocessed to at least partially remove sulfur and nitrogen. Preferably, the fraction after treatment contains up to 5 wppm of sulfur and up to 1 wppm of nitrogen. $C_4-$ hydrocarbons are removed from zone 111 via line 113. The remaining fraction is removed from zone 111 via line 115 and transferred to column 117 where the feed is fractionated to form a $C_5-$ hydrocarbon fraction and $C_6+$ hydrocarbon fraction. The $C_5-$ hydrocarbon fraction is withdrawn from column 117 via line 119. The $C_6+$ hydrocarbon fraction is withdrawn from column 117 via line 121 and introduced into zone 123 where the fraction is treated to at least partially remove dienes and olefins. After treatment, the fraction preferably contains up to 2500 wppm of olefins and dienes. The fraction is then withdrawn from zone 123 via line 125 and introduced into column 127 where the feed is fractionated to form a fraction containing benzene and benzene coboilers and a $C_7+$ aromatic fraction. The $C_7+$ aromatic fraction is removed from column 127 via line 129. The benzene/benzene coboiler fraction is withdrawn from column 127 via line 131 and introduced into propylation zone 133. Propylene is introduced into propylation zone 133 via line 135 and is reacted with the benzene to form cumene. Low molecular weight molecules, such as propylene and propane, are withdrawn from propylation zone 133 via line 137. Cumene-containing product is withdrawn from propylation zone 133 via line 139 and introduced into column 141. In column 141, the cumene-containing product is fractionated to form a $C_8-$ fraction and a $C_9+$ fraction comprised of cumene and polypropylbenzenes. The $C_8-$ fraction is withdrawn from column 141 via line 143 and is either removed via line 145 or recycled via line 131 to propylation zone 133. The $C_9+$ fraction is withdrawn from column 141 via line 147 and introduced into column 149. In Column 149, the $C_9+$ fraction is fractionated into a high purity cumene product fraction and a $C_{10}+$ fraction comprised of polypropylbenzenes. The $C_{10}+$ fraction is withdrawn from column 149 via line 153. Recovered polypropylbenzenes have a high octane rating and are available for upgrading the value of mogas pool (can be blended into gasoline to increase its octane). The high purity cumene product fraction is withdrawn from column 149 via line 151 and recovered without need of further purification. The cumene product will usually have a purity that exceeds 99.50 percent by weight based on the total weight of the product.

Figure 4:
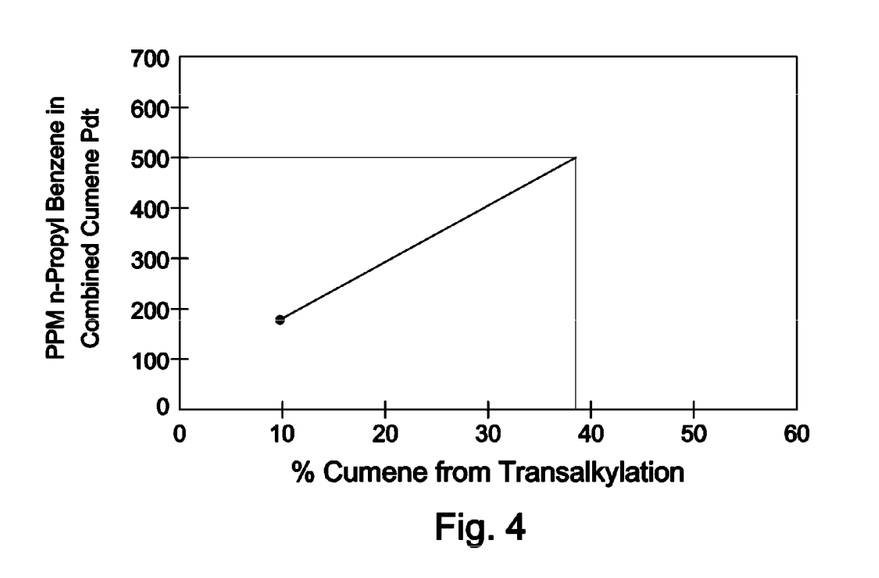
FIG. 4 is a graph plotting amounts of n-propylbenzene in combined product versus cumene contributed from transalkylation.

Although recovered polypropylbenzenes can be transalkylated with benzene to form cumene, it is preferred that the transalkylation product not be used in producing high purity cumene because the transalkylation can result in the formation of substantial amounts of n-propylbenzene, e.g., 1200 to 3000 wppm of n-propylbenzene. Combination of transalkylation product with the propylation product can result in the formation of cumene product having less than desired purity. FIG. 4 is a graph showing the result of combining a transalkylation product containing 1200 wppm of n-propylbenzene with cumene product containing 80 wppm of n-propylbenzene and formed in the propylation zone. As shown in FIG. 4, for a cumene product having a purity of 99.98 percent, the cumene product will be off specification if it contains more than 10 percent of the transalkyation product.

Propylation Catalyst

In a preferred embodiment, the catalyst used in propylating benzene will be acid-active catalyst comprising a crystalline MCM-22 family material. These molecular sieves are described in detail in "Atlas of Zeolite Framework Types", eds. Ch. Baerlocher, W. H. Meier, and D. H. Olson, Elsevier, Fifth Revised Edition, 2001, which is hereby incorporated by reference. Examples of MCM-22 family molecular sieves include MCM-22, MCM-36, MCM-49, MCM-56, ITQ-1, SSZ-25, and PSH-3. Preferably, the molecular sieve is MCM-22, and, most preferably, the molecular sieve is aluminosilicate MCM-22.

The acid-active catalyst used in this disclosure will usually have an alpha value in the range of from about 1 to about 1000, preferably from about 10 to about 1000, more preferably from about 100 to about 1000.

In some aspects, the acid-active catalyst used in this disclosure may comprise a medium pore molecular sieve having a Constraint Index of 2-12 (as defined in U.S. Pat. No. 4,016,218), including ZSM-5, ZSM-11, ZSM-12, ZSM-22, ZSM-23, ZSM-35, and ZSM-48. ZSM-5 is described in detail in U.S. Pat. Nos. 3,702,886 and Re. 29,948. ZSM-11 is described in detail in U.S. Pat. No. 3,709,979. ZSM-12 is described in U.S. Pat. No. 3,832,449. ZSM-22 is described in U.S. Pat. No. 4,556,477. ZSM-23 is described in U.S. Pat. No. 4,076,842. ZSM-35 is described in U.S. Pat. No. 4,016,245. ZSM-48 is more particularly described in U.S. Pat. No. 4,234,231. The entire contents of all the above patent specifications are incorporated herein by reference.

In some other aspects, the acid-active catalyst used in this disclosure may comprise a large pore molecular sieve having a Constraint Index of less than 2. Suitable large pore molecular sieves include zeolite beta, zeolite Y, Ultrastable Y (USY), Dealuminized Y (Deal Y), mordenite, ZSM-3, ZSM-4, ZSM-18, a MCM-22 family material, and ZSM-20. Zeolite ZSM-14 is described in U.S. Pat. No. 3,923,636. Zeolite ZSM-20 is described in U.S. Pat. No. 3,972,983. Zeolite beta is described in U.S. Pat. Nos. 3,308,069, and Re. No. 28,341. Low sodium Ultrastable Y molecular sieve (USY) is described in U.S. Pat. Nos. 3,293,192 and 3,449,070. Dealuminized Y zeolite (Deal Y) may be prepared by the method found in U.S. Pat. No. 3,442,795. Zeolite UHP-Y is described in U.S. Pat. No. 4,401,556. Rare earth exchanged Y (REY) is described in U.S. Pat. No. 3,524,820. Mordenite is a naturally occurring material but is also available in synthetic forms, such as TEA-mordenite (i.e., synthetic mordenite prepared from a reaction mixture comprising a tetraethylammonium directing agent). TEA-mordenite is disclosed in U.S. Pat. Nos. 3,766,093 and 3,894,104. The entire contents of all the above patent specifications are incorporated herein by reference.

In some embodiments, the acid-active catalyst may comprise a mixture of at least one medium pore molecular sieve having a Constraint Index of 2-12 and at least one large pore molecular sieve having a Constraint Index of less than 2.

The molecular sieve present in the catalyst will usually have an alpha value in the range of from about 100 to about 1000. The alpha value is a measure of molecular sieve acidic functionality and is described together with details of its measurement in U.S. Pat. No. 4,016,218 and in J. Catalysis, Vol. VI, pp. 278-287 (1966) and reference is made to these for such details. Higher alpha values correspond with a more active cracking catalyst.

The transalkylation catalyst may comprise a medium pore molecular sieve having a Constraint Index of 2-12 (as defined in U.S. Pat. No. 4,016,218), including ZSM-5, ZSM-11, ZSM-12, ZSM-22, ZSM-23, ZSM-35, and ZSM-48. ZSM-5, a large pore molecular sieve having a Constraint Index of less than 2. Suitable large pore molecular sieves include zeolite beta, MCM-22 family material, zeolite Y, Ultrastable Y (USY), Dealuminized Y (Deal Y), mordenite, ZSM-3, ZSM-4, ZSM-18, and ZSM-20 or any combination thereof.

The Constraint Index is a convenient measure of the extent to which an aluminosilicate or molecular sieve provides controlled access to molecules of varying sizes to its internal structure. For example, aluminosilicates which provide a highly restricted access to and egress from its internal structure have a high value for the constraint index, and aluminosilicates of this kind usually have pores of small size, e.g. less than 5 Angstroms. On the other hand, aluminosilicates which provide relatively free access to the internal aluminosilicate structure have a low value for the constraint index, and usually pores of large size. The method by which Constraint Index may be determined is described fully in U.S. Pat. No. 4,016,218, which is incorporated herein by reference.

Usually the crystalline molecular sieve will be combined with binder material resistant to the temperature and other conditions employed in the process. Examples of suitable binder material include clays, alumina, silica, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The molecular sieve may also be composited with zeolitic material such as the zeolitic materials which are disclosed in U.S. Pat. No. 5,993,642, which is hereby incorporated by reference.

The relative proportions of molecular sieve and binder material will vary widely with the molecular sieve content ranging from between about 1 to about 99 percent by weight, more preferably in the range of about 10 to about 70 percent by weight of molecular sieve, and still more preferably from about 40 to about 70 percent.

Aromatization

Aromatization will usually be carried out by the dehydrocyclo-oligomerization of $C_2$-$C_5$ aliphatics, catalytic reforming of naphtha, or the cracking of hydrocarbons.

Dehydrocyclo-oligomerization involves converting $C_2$-$C_5$ aliphatic hydrocarbons to aromatic hydrocarbons. The process is carried out by contacting $C_2$-$C_5$ aliphatic hydrocarbons in an aromatization zone and in the presence of a catalyst suitable for dehydrocyclodimerization and under conditions effective to produce an aromatics product comprising benzene and/or toluene. The dehydrocyclodimerization process increases carbon chain length by oligomerization, promotes cyclization, and dehydrogenates cyclics to their respective aromatics.

The feedstream used in the dehydrocyclo-oligomerization process will contain at least one aliphatic hydrocarbon containing 2 to about 5 carbon atoms. The aliphatic hydrocarbons may be open chain, straight chain, or cyclic. Examples of such hydrocarbons include ethane, ethylene, propane, propylene, n-butane, n-butenes, isobutane, isobutene, butadiene, straight and branched pentane, pentene, and pentadiene. Dehydrocyclo-oligomerization conditions will vary depending on such factors as feedstock composition and desired conversion. A desired range of conditions for the dehydrocyclodimerization of the aliphatic hydrocarbons to aromatics include a temperature from about 350° to about 750° C., a pressure from about 101.3 kPa-a to about 10.13 MPa-a, and weight hour space velocity from about 0.2 to about 8. It is understood that, as the average carbon number of the feed increases, a temperature in the lower end of temperature range is required for optimum performance and conversely, as the average carbon number of the feed decreases, the higher the required reaction temperature.

The catalyst used in the dehydrocyclo-oligomerization reaction will preferably comprise an intermediate pore size molecular sieve. Intermediate pore size molecular sieves have a pore size from about 5 to about 7 Å and include, for example, AEL, AFI, MWW, MFI, MEL, MFS, MEI, MTW, EUO, MTT, HEU, FER, and TON structure type molecular sieves. These materials are described in "Atlas of Zeolite Structure Types", eds. W. H. Meier, D. H. Olson, and Ch. Baerlocher, Elsevier, Fourth Edition, 1996, which is hereby incorporated by reference. Examples of suitable intermediate pore size molecular sieves include ZSM-5, ZSM-11, ZSM-12, ZSM-22, ZSM-23, ZSM-34, ZSM-35, ZSM-38, ZSM-48, ZSM-50, ZSM-57, MCM-22, MCM-49, MCM-56, and SAPO-5. Preferred molecular sieves are SAPO-11, as well as titanosilicate, gallosilicate, aluminosilicate, and gallium-containing aluminosilicate molecular sieves having a MFI structure.

Usually the molecular sieve will be combined with binder material resistant to the temperature and other conditions employed in the process. Suitable binder material and relative proportions of molecular sieve and binder material are the same as those described above for the catalyst used for the propylation of benzene.

When the hydrocarbon composition feed used in the present disclosure is made from reformate produced by catalytic reforming, the reformate will usually be formed by contacting a $C_6$+ paraffinic feed, e.g., naphtha, with a reforming catalyst under reforming conditions to produce a reaction product comprising benzene and other hydrocarbons. The reformate is formed under typical reforming conditions designed to promote dehydrogenation of naphthenes, isomerization of paraffinic hydrocarbons and dehydrocyclization of non-aromatic hydrocarbons.

Substantially any hydrocarbon feed containing $C_6$+ paraffins, e.g., naphtha, can be utilized as feedstock for naphtha reforming. The naphtha will generally comprise $C_6$-$C_9$ aliphatic hydrocarbons. The aliphatic hydrocarbons may be straight or branched chain acyclic hydrocarbons, and particularly paraffins such as heptane.

Catalysts suitable for use in catalytic reforming include acidic reforming catalysts (bifunctional catalysts) and non-acidic reforming catalysts (monofunctional catalysts).

Acidic reforming catalysts usually comprise a metallic oxide support having disposed therein a Group 8, 9, or 10 metal. Suitable metallic oxide supports include alumina and silica. Preferably, the acidic reforming catalyst comprises a metallic oxide support having disposed therein in intimate admixture a Group 8, 9, or 10 metal (preferably platinum) and a metal promoter, such as rhenium, tin, germanium, cobalt, nickel, iridium, rhodium, ruthenium and combinations thereof. More preferably, the acidic reforming catalyst comprises an alumina support, platinum, and rhenium or platinum and tin on an alumina support.

Non-acidic or monofunctional reforming catalysts will comprise a non-acidic molecular sieve, e.g., zeolite, and one or more hydrogenation/dehydrogenation components. Examples of suitable molecular sieves include MFI structure type, e.g., silicalite, and molecular sieves having a large pore size, e.g., pore size from about 7 to 9 Angstroms. Examples of large pore molecular sieves include LTL, FAU, and *BEA structure types. Examples of specific molecular sieves include zeolite L, zeolite X, zeolite Beta, zeolite Y, and ETS-10.

The reforming catalysts will contain one or more hydrogenation/dehydrogenation metals, e.g., Group 7 metals, such as rhenium, and Group 8, 9, or 10 metals, such as nickel, ruthenium, rhodium, palladium, iridium or platinum. The preferred Group 8, 9, or 10 metal is platinum. Also, the nonacidic catalyst can contain a metal promoter such as tin.

The amount of hydrogenation/dehydrogenation metal present on the non-acidic catalyst will usually be from about 0.1% to about 5.0% of hydrogenation/dehydrogenation metal based on the weight of the catalyst. The metal can be incorporated into the zeolite during synthesis of the zeolite, by impregnation, or by ion exchange of an aqueous solution containing the appropriate salt. By way of example, in an ion exchange process, platinum can be introduced by using cationic platinum complexes such as tetraammine-platinum (II) nitrate.

The non-acidic catalyst will usually include a binder. The binder can be a natural or a synthetically produced inorganic oxide or combination of inorganic oxides. Typical inorganic oxide supports which can be used include clays, alumina, and silica, in which acidic sites are preferably exchanged by cations that do not impart strong acidity.

The reforming process can be continuous, cyclic or semi-regenerative. The process can be in a fixed bed, moving bed, tubular, radial flow or fluid bed.

Conditions for reforming conditions include temperatures of at least about 400° C. to about 600° C. and pressures from about 344.7 kPa-a to about 3.447 MPa-a, a mole ratio of hydrogen to hydrocarbons from 1:1 to 10:1 and a liquid hour space velocity of between 0.3 and 10.

When the hydrocarbon composition feed used in the present disclosure is made from reformate produced by steam cracking, the reformate will usually be formed by contacting a $C_6+$ paraffinic feed, e.g., naphtha, and steam under steam cracking conditions to produce a reaction product comprising benzene and other hydrocarbons. The reformate is formed under typical steam cracking conditions designed to promote thermal conversion of paraffins to light olefins and aromatics.

Substantially any hydrocarbon feed containing $C_2+$ paraffins, e.g., ethane, propane, butanes, naphtha, distillate, atmospheric gas oil, vacuum gas oil, and/or any combination can be utilized as feedstock for steam cracking. The naphtha will generally comprise $C_6$-$C_9$ non-aromatic hydrocarbons. The non-aromatic hydrocarbons may be straight or branched chain cyclic and acyclic hydrocarbons, and particularly cyclic hydrocarbons such as methylcyclopentadiene.

The hydrocarbon composition will contain from about 1 to about 75 percent by weight of at least one benzene coboiler, i.e., $C_6+$ non-aromatic hydrocarbons having a boiling point within 10° C. at a pressure of about 101.3 kPa-a of the boiling point of benzene. Some hydrocarbon compositions will contain different amounts of benzene coboilers, e.g., about 5 to about 60 percent by weight of the at least one benzene coboiler or from about 10 to about 50 percent by weight of the at least one benzene coboiler. Also in some hydrocarbon compositions, the $C_6+$ non-aromatic hydrocarbons present in the hydrocarbon composition will have a boiling point within 5° C. at a pressure of about 101.3 kPa-a of the boiling point of benzene.

Examples of benzene coboilers that can be present in the hydrocarbon composition feed to the propylation unit include cyclopentane, cyclohexane, methylcyclopentane, 2-methylhexane, 3-methylhexane, 2,3-dimethylpentane, 2,4-dimethylpentane, and dimethylcyclopentane.

Feed Pretreatment

The hydrocarbon composition feed used in the process of the present disclosure may contain impurities such as, for example, olefins, dienes, sulfur-containing compounds, nitrogen-containing compounds, and combinations thereof. Preferably, at least a portion of one or more of these impurities is removed from the hydrocarbon composition feed before propylation of benzene to extend the cycle length of the catalyst and to reduce the formation of cumene co-boilers in the product of the propylation reactor.

Techniques for removing these impurities are known to persons skilled in the art. Nitrogen-containing and sulfur-containing impurities can be removed by hydroprocessing. Hydroprocessing techniques are well known in the art and are often required to enable steam cracker naphtha to be blended into gasoline that meets U.S. low sulfur gasoline specifications. Hydroprocessing is carried out by treating a hydrocarbon feed with hydrogen in the presence of a supported catalyst at hydrotreating conditions. The catalyst is usually comprised of a Group 6 metal with one or more Group 8, 9, or 10 metals as promoters on a refractory support. In a preferred embodiment, steam cracker naphtha is hydrotreated to reduce sulfur levels to less than 5 wppm, nitrogen levels to less than 1 wppm, and olefin and diene levels to less than 2500 wppm. Hydroprocessing produces a naphtha from steam cracking with very similar levels of impurities to the naphtha produced from naphtha reforming. Techniques for subsequently removing the olefins and dienes (from either reformate or hydroprocessed steam cracker naphtha) are disclosed in U.S. Pat. Nos. 6,781,023 and 6,500,996, which are incorporated by reference. A preferred technique for removing olefins and dienes involves contacting the hydrocarbon composition feed containing olefins/dienes with a crystalline molecular sieve catalyst comprising MCM-22.

Nitrogen-containing and sulfur-containing impurities can also be removed by contacting the nitrogen-containing and sulfur-containing hydrocarbon composition feed with an absorbent under absorption conditions effective to remove at least a portion of the nitrogen-containing/sulfur-containing impurities. Example of suitable absorbents include clay materials and alumina compounds. Preferred absorption conditions include a temperature of from ambient to 500° C., more preferably from ambient to 200° C., or most preferably from ambient to 100° C.; a pressure sufficient to maintain liquid phase conditions; a weight hourly space velocity from 0.5 $hr^{-1}$ to about 100 $hr^{-1}$, more preferably from about 0.5 $hr^{-1}$ to about 10 $hr^{-1}$, most preferably from 1.0 $hr^{-1}$ to 4.0 $hr^{-1}$ depending upon the hydrocarbon composition feed being treated.

Process

Suitable alkylating agent(s) that may be used in this disclosure comprise alkene compound(s), alcohol compound(s), and/or alkylbenzene(s), and mixtures thereof. Other suitable alkylating agents that may be useful in the process of this disclosure generally include any aliphatic or aromatic organic compound having one or more available alkylating aliphatic groups capable of reaction with the alkylatable aromatic compound. Examples of suitable alkylating agents comprise $C_3$ olefin; $C_3$ alkanols; $C_2$-$C_{20}$ ethers, e.g., $C_2$-$C_5$ ethers including dimethylether and diethylether; aldehydes such as formaldehyde, acetaldehyde, propionaldehyde, butyraldehyde, and n-valeraldehyde; and alkyl halides such as methyl chloride, ethyl chloride, the propyl chlorides, the butyl chlorides, and the pentyl chlorides, polyalkylated aromatic compound(s), e.g., bi-alkylated benzenes (e.g., bi-ethylbenzene(s) or bi-isopropylbenzenes) and tri-alkylated benzene(s) (e.g., tri-ethylbenzenes or tri-isopropylbenzenes), and so forth. Thus the alkylating agent may preferably be selected from the group consisting of $C_2$-$C_5$ olefins, $C_1$-$C_5$ alkanols, bi-ethylbenzene(s), bi-isopropylbenzene(s), tri-ethylbenzene(s) and/or tri-isopropylbenzene(s). The alkylating agent includes a concentrated alkene feedstock (e.g., polymer grade olefins) and a dilute alkene feedstock (e.g., catalytic cracking off-gas). Preferably, the alkylating agent includes propylene, propyl-alcohol, polypropylbenzene, or any mixture thereof.

In some embodiments, the process of the present disclosure is carried out in at least partial liquid phase at conditions that include a temperature of up to about 250° C., e.g., up to about 170° C., e.g., from about 10° C. to about 170° C.; in the range of from about 110° C. to about 170° C., a pressure sufficient to maintain the mixture of benzene and propylene in at least partial liquid phase, usually at least 101.3 kPa-a, at least 689.5 kPa-a, e.g., from about 689.5 kPa-a to about 6.89 MPa-a, a mole ratio of propylene to benzene in the range of from about 0.001:1 to about 1:1, preferably from about 0.01 to 0.5; and a feed weight hourly space velocity in the range of from about 0.1 to about 250 $hr^1$, preferably from about 1 to 50 $hr^1$, more preferably from about 5 to 10 $hr^1$. Preferred conditions include a temperature of from about 120° C. to about 150° C., a pressure of from about 1.37 MPa-a to about 2.76 MPa-a, a mole ratio of propylene to benzene of from about 0.01:1 to about 0.5:1, and a feed weight hourly space velocity of from about 0.5 and about 2 hr$^1$. More preferably, the mole ratio of propylene to benzene is in the range of from about 0.02:1 to about 0.04:1. Most preferably, mole ratio of propylene to benzene is about 0.03.

In some embodiments, the process of the present disclosure is carried out by maintaining the mixture of benzene and propylene in substantially liquid phase, optionally in liquid phase, at conditions that include a temperature of up to about 250° C., e.g., up to about 170° C., e.g., from about 10° C. to about 170° C.; in the range of from about 110° C. to about 170° C., a pressure sufficient to maintain the mixture of benzene and propylene in substantially liquid phase, optionally in liquid phase, usually at least 689.5 kPa-a, e.g., from about 689.5 kPa-a to about 6.89 MPa-a, a mole ratio of propylene to benzene in the range of from about 0.001:1 to about 1:1, preferably from about 0.01 to 0.5; and a feed weight hourly space velocity in the range of from about 0.1 to about 250 hr$^1$, preferably from about 1 to 50 hr$^1$, more preferably from about 5 to 10 hr$^1$. Preferred conditions include a temperature of from about 120° C. to about 150° C., a pressure of from about 1.37 MPa-a to about 2.76 MPa-a, a mole ratio of propylene to benzene of from about 0.01:1 to about 0.5:1, and a feed weight hourly space velocity of from about 0.5 and about 2 hr$^1$. More preferably, the mole ratio of propylene to benzene is in the range of from about 0.02:1 to about 0.4:1. Most preferably, mole ratio of propylene to benzene is about 0.03.

The alkylating agent, e.g., propylene, to benzene ratios specified for use in the process of the present disclosure refers to the mole ratio of alkylating agent, e.g., propylene, to benzene at the reactor inlet. For example, in case of a reactor having more than one catalyst bed, e.g., four beds, with propylene feed being injected into each bed, the mole ratio of propylene to benzene injected into each bed will be within the specified range, i.e., propylene to benzene mole ratio will be within a range defined by a lower number and a high number. For any specific range defined by a lower number and a high number, the lower number will be equal or lower than the higher end number, A range useful for this disclosure may be defined by any combination of two numbers selected from the group consisting of 0.001:1, 0.01:1, 0.015:1, 0.2:1, 0.025:1, 0.3:1; 0.31:1, 0.35:1, 0.4:1, 0.45:1, 0.5:1, 0.55:1, 0.6:1, 0.65:1, 0.7:1, 0.75:1, 0.8:1, 0.85:1, 0.9:1, 0.95:1, and 1:1. Examples of typical range are 0.001:1 to 0.75:1, 0.01:1 to 0.6:1; 0.02:1 to 0.5:1; 0.02:1 to 0.4:1; 0.02:1 to 0.3:1; and 0.02:1 to 0.1:1.

The process of the present disclosure produces a cumene product that contains at least 99.50 weight percent of cumene based on the weight of the product. Preferably, the process of the present disclosure produces an cumene product that contains at least 99.90 weight percent of cumene based on the weight of the product, more preferably the cumene product has a purity of at least 99.95 weight percent, and most preferably the cumene product has a purity of at least 99.985 weight percent. To further enhance the purity of the cumene product, the product can be blended with higher purity cumene product. For example, an cumene product having 99.95 weight percent purity can be increased to 99.97 weight percent purity by blending appropriate amounts of higher purity cumene product (100 percent cumene product) with the 99.95 purity product.

Distillation temperatures for separations, e.g., separation of polypropylbenzenes from cumene, are known to persons skilled in the art and will depend upon the composition of the feeds, e.g., composition of the polypropylbenzene/cumene feed.

The process of the present disclosure includes recovery of polypropylbenzenes as a separate fraction and use of the recovered polypropylbenzenes as a gasoline blending component to increase the octane value of gasoline.

The effluent from the reaction zone comprises the desired cumene, unreacted benzene, any unreacted propylene (propylene conversion is expected to be at least 90 mol. %, preferably, about 98-99.9999 mol. %) and the alkane component and the other impurities. In one embodiment, at least a portion of the effluent is fed to another reaction zone where additional propylene is added for reaction with the unreacted benzene with an alkylation catalyst. Furthermore, at least a portion the effluent from any of the reaction zone(s) may be fed directly or indirectly to a transalkylation unit.

In addition to, and upstream of, the reaction zones, a by-passable reactive or unreactive guard bed may normally be located in a reactor separate from the alkylation reactor. Such guard bed may also be loaded with an alkylation or transalkylation catalyst, which may be the same or different from the catalyst used in the reaction zone(s). Such guard bed is maintained from under ambient conditions, or at suitable alkylation or transalkylation conditions. At least a portion of benzene, and optionally at least a portion of the propylene, are passed through the unreactive or reactive guard bed prior to entry into the reaction zone. These guard beds not only serve to affect the desired alkylation reaction, but is also used to remove any reactive impurities in the hydrocarbon composition feeds, such as nitrogen compounds, which could otherwise poison the remainder of the alkylation or transalkylation catalyst. The catalyst in the reactive or unreactive guard bed may therefore subject to more frequent regeneration and/or replacement than the remainder of the alkylation or transalkylation catalyst, and hence the guard bed is typically provided with a by-pass circuit so that the alkylation feed(s) may be fed directly to the series connected reaction zones in the reactor while the guard bed is out of service. The reactive or unreactive guard bed may be operated in co-current upflow or downflow operation.

The reaction zone(s) used in the process of the present invention is typically operated so as to achieve essentially complete conversion of the propylene. However, for some applications, it may be desirable to operate at below 100% propylene conversion. The employment of a separate finishing reactor downstream of the reaction zone(s) may be desirable under certain conditions. The finishing reactor would also contain alkylation or transalkylation catalyst, which could be the same or different from the catalyst used in other reaction zones in the alkylation or transalkylation reactor(s) and may be maintained under at least partially liquid phase or alternately vapor phase alkylation or transalkylation conditions. The polyalkylated aromatic compounds in the effluents may be separated for transalkylation with alkylatable aromatic compound(s). The alkylated aromatic compound is made by transalkylation between polyalkylated aromatic compounds and the alkylatable aromatic compound.

The alkylation or transalkylation reactor(s) used in the process of the present invention may be highly selective to the desired monoalkylated product, such as cumene, but typically produces at least some polyalkylated species. In one embodiment, at least a portion of the effluent from the final alkylation reaction zone is subjected to a separation step to recover polyalkylated aromatic compound(s). In another embodiment, at least a portion of the polyalkylated aromatic compound is supplied to a transalkylation reactor which may be separate from the alkylation reactor. The transalkylation reactor produces an effluent which contains additional monoalkylated product by reacting the polyalkylated species with an alkylatable aromatic compound. At least a portion of these effluents may be separated to recover the alkylated aromatic compound (monoalkylated aromatic compound and/or polyalkylated aromatic compound).

Where the alkylation system includes a reactive guard bed, it is maintained under at least partial in liquid phase conditions. The guard bed will preferably operate at a temperature of from about 120 to 285° C., preferably, a temperature of from about 150 to 260° C., a pressure of 689 to 4601 kPa-a), preferably, a pressure of 1500 to 4137 kPa-a, a WHSV based on total propylene and the total amount of catalyst for the overall reactor of 0.1 to 10 h$^{-1}$, preferably, 0.2 to 2 h$^{-1}$, more preferably, 0.5 to 1 h$^{-1}$, or a WHSV based on both total propylene and total benzene, and the total amount of catalyst for the overall reactor of 10 to 100 h$^{-1}$, preferably, 20 to 50 h$^{-1}$, and a molar ratio of benzene to propylene from about 1 to about 100, preferably from about 20 to about 80.

The transalkylation reaction may take place under at least partially in liquid phase conditions. Particular conditions for carrying out the at least partially in liquid phase transalkylation of polyalkylated aromatic compound(s), e.g., polyisopropylbenzene(s), with benzene may include a temperature of from about 100° to about 300° C., a pressure of 696 to 4137 kPa-a, a WHSV based on the weight of the polyalkylated aromatic compound(s) feed to the alkylation reaction zone of from about 0.5 to about 100 hr$^{-1}$ and a molar ratio of benzene to polyalkylated aromatic compound(s) of from 1:1 to 30:1, preferably, 1:1 to 10:1, more preferably, 1:1 to 5:1.

In another embodiment, the transalkylation reaction may take place under vapor phase conditions. Particular conditions for carrying out the vapor phase transalkylation of polyalkylated aromatic compound(s), polyisopropylbenzene(s), with benzene may include a temperature of from about 350 to about 450° C., a pressure of 696 to 1601 kPa-a, a WHSV based on the weight of the polyalkylated aromatic compound(s) feed to the reaction zone of from about 0.5 to about 20 hr$^{-1}$, preferably, from about 1 to about 10 hr$^{-1}$, and a molar ratio of benzene to polyalkylated aromatic compound(s) of from 1:1 to 5:1, preferably, 2:1 to 3:1.

In some embodiments, this disclosure relates to:
1. A hydrocarbon composition that is substantially free of C$_4$– hydrocarbons and C$_7$+ aromatic hydrocarbons, said hydrocarbon composition comprising:
   (i) benzene;
   (ii) from about 1 to about 75 percent by weight based on the weight of the hydrocarbon composition, of at least one C$_6$+ non-aromatic hydrocarbon having a boiling point within 10° C. at a pressure of about 101.3 kPa-a of the boiling point of benzene;
   (iii) up to 5, 4, 3, 2 or 1 wppm of sulfur;
   (iv) up to 0.2, 0.4, 0.6, 0.8 or 1 wppm of nitrogen; and
   (v) up to 250, 500, 1000, 1500, 2000 or 2500 wppm of olefins and dienes.
2. The hydrocarbon composition recited in any preceding Paragraph, wherein said at least one C6+ non-aromatic hydrocarbon is present in said hydrocarbon composition in an amount from about 5 to about 60 percent by weight based on the weight of said hydrocarbon composition.
3. The hydrocarbon composition recited in any preceding Paragraph, wherein said boiling point of said at least C6+ non-aromatic hydrocarbons is within 5° C. at a pressure of about 101.3 kPa-a of the boiling point of benzene.
4. The hydrocarbon composition recited in any preceding Paragraph, wherein said at least one C6+ non-aromatic hydrocarbon is selected from the group consisting of cyclohexane, methylcyclopentane, 2-methylhexane, 3-methylhexane, 2,3-dimethylpentane, 2,4-dimethylpentane, dimethylcyclopentane, and mixtures thereof.
5. The hydrocarbon composition recited in any preceding Paragraph, wherein said hydrocarbon composition is produced from a product formed by steam cracking of naphtha.
6. The hydrocarbon composition recited in Paragraph 5, wherein said product formed by steam cracking of naphtha comprises:
   (i) C5– hydrocarbons;
   (ii) benzene;
   (iii) C7+ aromatic hydrocarbons;
   (iv) from about 1 to about 75 percent by weight of at least one C6+ non-aromatic hydrocarbon having a boiling point within 10° C. at a pressure of about 101.3 kPa-a of the boiling point of benzene;
   (v) greater than 5, 4, 3, 2 or 1 wppm of sulfur;
   (vi) greater than 0.2, 0.4, 0.6, 0.8 or 1 wppm of nitrogen; and
   (vii) greater than 250, 500, 1000, 1500, 2000 or 2500 wppm of olefins and dienes.
7. The hydrocarbon composition recited in Paragraph 6, wherein said hydrocarbon composition comprises a C6 hydrocarbon fraction recovered from said product formed by steam cracking naphtha, said C6 hydrocarbon fraction being recovered by the steps of:
   (a) removing C4– hydrocarbons from said product;
   (b) removing sulfur and nitrogen from the product of step (a) to produce a resulting product containing up to 5, 4, 3, 2 or 1 wppm of sulfur and up to 0.2, 0.4, 0.6, 0.8 or 1 wppm of nitrogen;
   (c) fractionating in a distillation zone the resulting product of step (b) to form a C5-fraction and a C6+ fraction:
   (d) withdrawing said C6+ fraction from said distillation zone;
   (e) treating said C6+ fraction to remove olefins and dienes from said C6+ fraction to form a resulting C6+ fraction containing 250, 500, 1000, 1500, 2000 or 2500 wppm of olefins and dienes;
   (f) fractionating in a distillation zone the resulting C6+ fraction of step (e) to form a C6 fraction and a C7+ fraction; and
   (g) withdrawing said C6 fraction.
8. The hydrocarbon composition recited in any preceding paragraph, wherein said hydrocarbon composition is recovered from a reformate by a recovery process free of extracting step.
9. A process for producing an cumene product having a purity of at least 99.50 percent based on the weight of cumene present in the product using a hydrocarbon composition feed that has not undergone extraction, is substantially free of C4– hydrocarbons and C7+ aromatic hydrocarbons, and contains benzene and from about 1 to about 75 percent by weight of at least one C6+ non-aromatic hydrocarbon having a boiling point within 10° C. at a pressure of about 101.3 kPa-a of the boiling point of benzene, said process comprising:
   (a) alkylating the benzene with propylene in an alkylation reaction zone, said reaction zone is maintained under at least partial liquid phase conditions, with an acid-active catalyst comprising at least one of a crystalline MCM-22 family material and a zeolite beta molecular sieve at conditions that include a temperature in the range of from about 110° C. to about 170° C., a pressure sufficient to maintain the benzene in the liquid phase, a mole ratio of propylene to benzene in the range of from about 0.01:1 to about 0.75:1, and a feed weight hourly space velocity in the range of from about 0.1 to about 10 hr1; and
   (b) distilling the product of step (a) to produce an cumene product having a purity of at least 99.50 percent based on the weight of cumene present in said cumene product.

10. The process recited in Paragraph 9, wherein said hydrocarbon composition feed is produced from a reformate.

11. The process recited in Paragraph 10, wherein said reformate comprises: (i) C5-hydrocarbons; (ii) benzene; (iii) C7+ aromatic hydrocarbons; and (iv) from about 1 to about 75 percent by weight of at least one C6+ non-aromatic hydrocarbon having a boiling point within 10° C. at a pressure of about 101.3 kPa-a of the boiling point of benzene and said hydrocarbon composition feed is prepared from said reformate by removing by distillation the C4− hydrocarbons and said C7+ aromatic hydrocarbons from said reformate.

12. The process as recited in any one of Paragraphs 9-11, further comprising recovering polypropylbenzenes from the product of step (a).

13. The process as recited in Paragraph 12, wherein at least a portion of the recovered polypropylbenzenes is blended into gasoline.

14. The process recited in any one of Paragraphs 9-13, wherein the alkylation conditions include temperature of from about 120° C. to about 150° C., a pressure of from about 1.479 MPa-a to about 2.859 MPa-a, a mole ratio of propylene to benzene of from about 0.01:1 to about 0.5:1, and a feed weight hourly space velocity of from about 0.5 and about 2 hr1.

15. The process recited in any one of Paragraphs 9-14, wherein said mole ratio of propylene to benzene is from about 0.02:1 to about 0.4:1.

16. The process recited in Paragraph 15, wherein said mole ratio of propylene to benzene is about 0.03.

17. The process as recited in any one of Paragraphs 9-16, wherein said crystalline MCM-22 family material is selected from the group consisting of MCM-22, MCM-36, MCM-49, and MCM-56.

18. The process as recited in Paragraph 17, wherein said catalyst further comprises a binder.

19. The process recited in Paragraph 18, wherein said crystalline MCM-22 family material is MCM-22.

20. The process as recited in any one of Paragraphs 9-19, wherein said at least one C6+ non-aromatic hydrocarbon is selected from the group consisting of cyclohexane, methylcyclopentane, 2-methylhexane, 3-methylhexane, 2,3-dimethylpentane, 2,4-dimethylpentane, dimethylcyclopentane, and mixtures thereof.

21. The process recited in any one of Paragraphs 9-20, wherein said purity of said cumene product is at least 99.90 percent based on the weight of cumene present in the product.

22. The process recited in any one of Paragraphs 9-21, wherein said purity of said cumene product is at least 99.95 percent based on the weight of cumene present in the product.

23. The process recited in Paragraph 10, wherein said reformate is formed by catalytic reforming of naphtha.

24. The process recited in Paragraph 10, wherein said reformate is formed by the cracking of hydrocarbons.

25. The process recited in Paragraph 24, wherein said cracking is accomplished by steam cracking.

26. The process as recited in any one of Paragraphs 9-25, wherein said at least one C6+ non-aromatic hydrocarbon is present in said hydrocarbon composition feed in an amount of from about 10 to about 50 percent by weight of at least one C6+ non-aromatic hydrocarbon having a boiling point within 10° C. at a pressure of about 101.3 kPa-a of the boiling point of benzene.

27. The process as recited in any one of Paragraphs 9-26, wherein said hydrocarbon composition feed contains impurities selected from the group consisting of olefins, dienes, sulfur-containing compounds, nitrogen-containing compounds, and mixtures thereof and at least a portion of at least one of said impurities are removed from the hydrocarbon composition feed prior to contact with said catalyst.

28. The process as recited in any one of Paragraphs 9-27, wherein said hydrocarbon composition is substantially free of $C_4-$ hydrocarbons and $C_7+$ aromatic hydrocarbons and comprises:
   (i) benzene;
   (ii) from about 1 to about 75 percent by weight based on the weight of the hydrocarbon composition, of at least one C6+ non-aromatic hydrocarbon having a boiling point within 10° C. at a pressure of about 101.3 kPa-a of the boiling point of benzene;
   (iii) up to 1, 2, 3, 4 or 5 wppm of sulfur;
   (iv) up to 0.2, 0.4, 0.6, 0.8 or 1 wppm of nitrogen; and
   (v) up to 250, 500, 1000, 1500, 2000 or 2500 wppm of olefins and dienes.

29. A process for producing an cumene product having a purity of at least 99.50 percent based on the weight of cumene present in the product using a hydrocarbon composition produced from a reformate, said hydrocarbon composition has not undergone extraction, said process comprising:
   (a) providing a reformate that comprises: (i) C5− hydrocarbons; (ii) benzene; (iii) C7+ aromatic hydrocarbons; and (iv) from about 1 to about 75 percent by weight based on the weight of the reformate of at least one C6+ non-aromatic hydrocarbon having a boiling point within 10° C. at a pressure of about 101.3 kPa-a of the boiling point of benzene;
   (b) removing C4− hydrocarbons and the C7+ aromatic hydrocarbons from the reformate by distillation to from said hydrocarbon composition;
   (c) alkylating the benzene present in the hydrocarbon composition without extraction of the reformate with propylene under at least partial liquid phase with a catalyst comprising at least one of a crystalline MCM-22 family material and a zeolite beta molecular sieve at conditions that a temperature in the range of from about 110° C. to about 170° C., a pressure sufficient to maintain the benzene and the propylene mixture in at least partial liquid phase, a mole ratio of propylene to benzene in the range of from about 0.001:1 to about 0.75:1, and a feed weight hourly space velocity in the range of from about 0.1 to about 10 hr1; and
   (d) distilling the product of step (c) to produce an cumene product having a purity of at least 99.50 percent based on the weight of cumene present in the product.

30. The process recited in Paragraph 29, wherein the alkylation conditions include temperature of from about 120° C. to about 150° C., a pressure of from about 1.479 MPa-a to about 2.859 MPa-a, a mole ratio of propylene to benzene of from about 0.1:1 to about 0.5:1, and a feed weight hourly space velocity of from about 0.5 and about 2 hr$^1$.

31. The process recited in any one of Paragraphs 29-30, wherein said mole ratio of propylene to benzene is from about 0.2:1 to about 0.4:1.

32. The process recited in any one of Paragraphs 29-31, wherein said mole ratio of propylene to benzene is about 0.3.

33. The process as recited in any one of Paragraphs 29-32, wherein said crystalline MCM-22 family material is selected from the group consisting of MCM-22, MCM-36, MCM-49, and MCM-56.

34. The process as recited in Paragraph 33, wherein said crystalline MCM-22 family material is MCM-22.

35. The process recited in any one of Paragraphs 29-34, wherein said reformate is formed by catalytic reforming of naphtha.

36. The process recited in any one of Paragraphs 29-34, wherein said reformate is formed by the cracking of hydrocarbons.

37. The process recited in Paragraph 36, wherein said cracking is accomplished by steam cracking.

38. The process recited in any one of Paragraphs 29-37, wherein said purity of said cumene product is at least 99.90 percent based on the weight of cumene present in the product.
39. The process as recited any one of Paragraphs 29-38, wherein said hydrocarbon composition feed contains impurities selected from the group consisting of olefins, dienes, sulfur-containing compounds, nitrogen-containing compounds, and mixtures thereof and at least a portion of at least one of said impurities are removed from the hydrocarbon composition feed prior to contact with said catalyst.
40. The process as recited in Paragraph 39, wherein the hydrocarbon composition that is substantially free of $C_4$- hydrocarbons and $C_7$+ aromatic hydrocarbons and comprises:
  (i) benzene;
  (ii) from about 1 to about 75 percent by weight based on the weight of the hydrocarbon composition, of at least one C6+ non-aromatic hydrocarbon having a boiling point within 10° C. at a pressure of about 101.3 kPa-a of the boiling point of benzene;
  (iii) up to 5, 4, 3, 2 or 1 wppm of sulfur;
  (iv) up to 0.2, 0.4, 0.6, 0.8 or 1 wppm of nitrogen; and
  (v) up to 250, 500, 1000, 1500, 2000 or 2500 wppm of olefins and dienes.
41. The process as recited in any one of Paragraphs 29-40, wherein said at least one $C_6$+ non-aromatic hydrocarbon is present in said hydrocarbon composition feed in an amount of from about 10 to about 50 percent by weight of at least one $C_6$+ non-aromatic hydrocarbon having a boiling point within 10° C. at a pressure of about 101.3 kPa-a of the boiling point of benzene.

The following example illustrates certain embodiments of the present disclosure but is not intended to be construed as to be restrictive of the spirit and scope thereof.

Example 1

Figure 5:
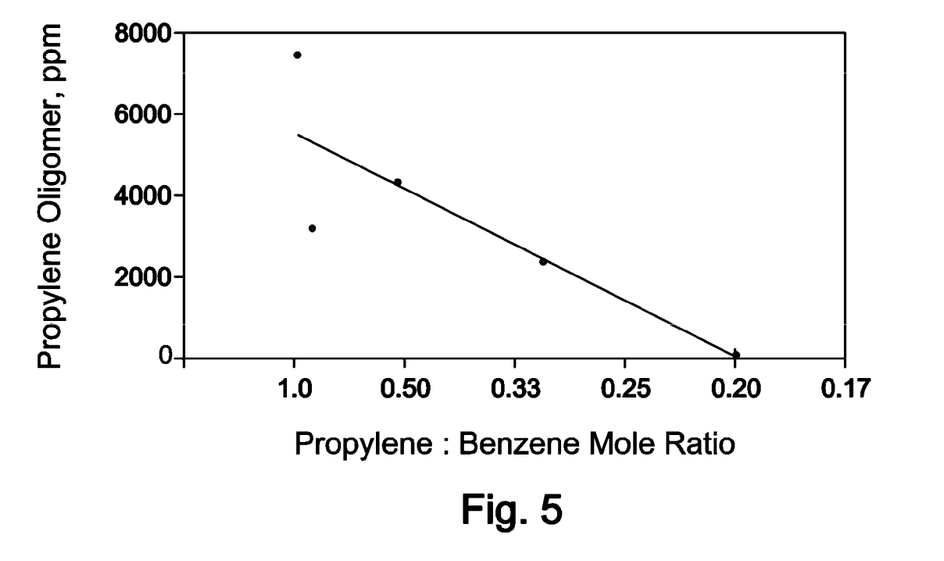
FIG. 5 is a graph illustrating results of Example 1.

Tests were carried out with a hydrocarbon composition feed comprised of 66 weight percent benzene and 34 percent by weight of 2-methyl-hexane. Propylene was present in the hydrocarbon composition feed in amounts such that the propylene to benzene mole ratio of the feed ranged from 0.20 to 1.0. The test was conducted by passing the feed over a MCM-22 catalyst at a temperature of 130° C. and at a pressure sufficient to maintain the benzene in the liquid phase. FIG. 5 plots propylene oligomer impurities and shows significantly lower propylene oligomer impurities in the practice of the present disclosure.

Example 2

Figure 6:
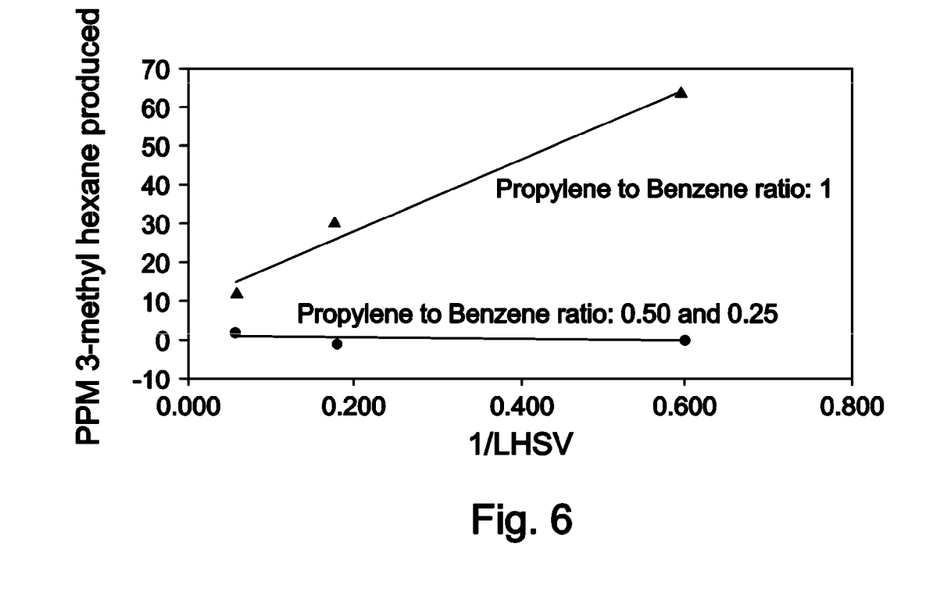
FIG. 6 is a graph illustrating results of Example 2.
Figure 7:
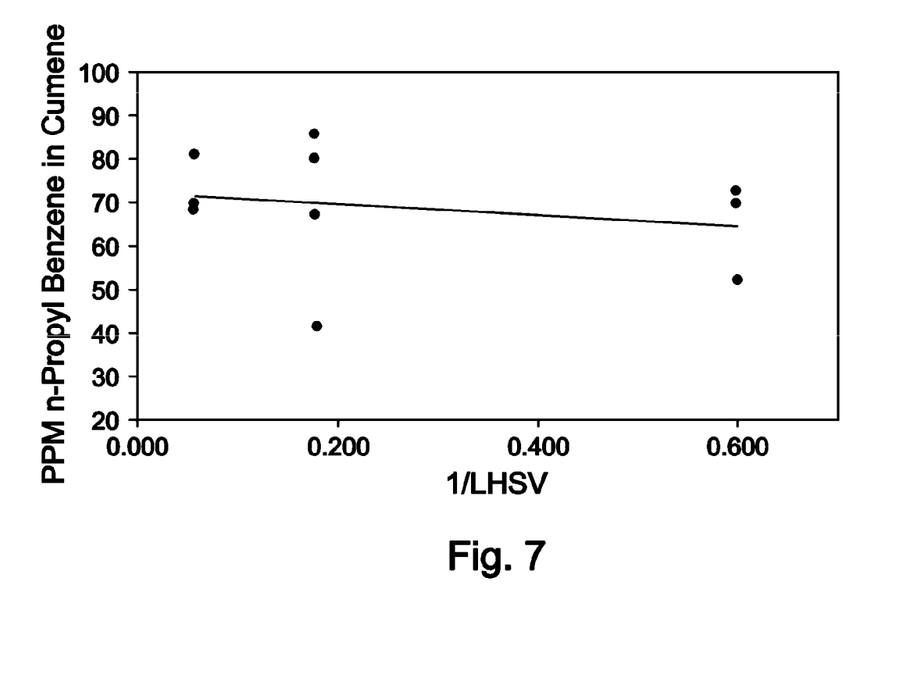
FIG. 7 is a graph illustrating results of Example 2.
Figure 8:
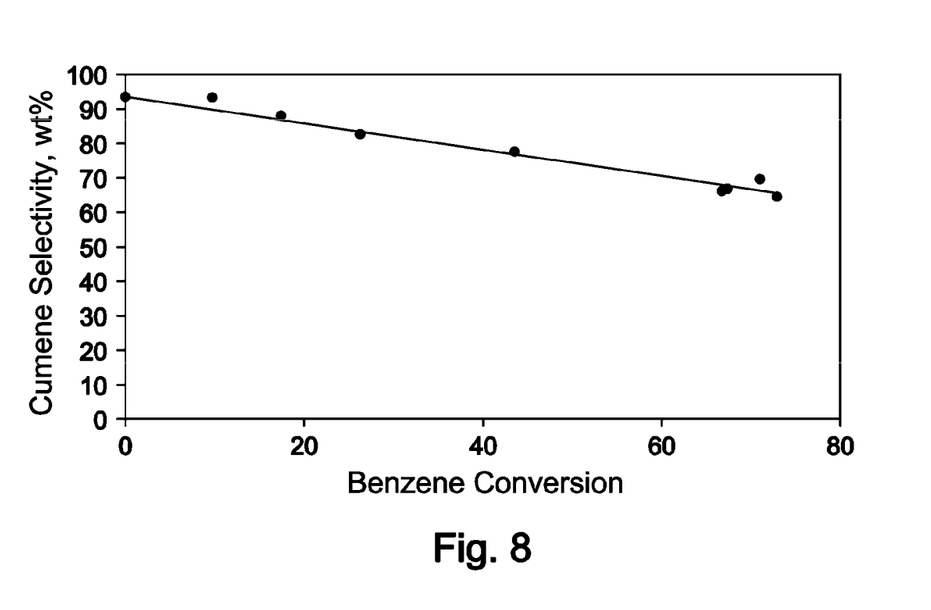
FIG. 8 is a graph illustrating results of Example 2.

Tests were carried out with a hydrocarbon composition feed that comprised 66 weight percent benzene and 34 percent by weight of 2-methyl-hexane. Propylene was present in the feed in varied amounts, i.e., the propylene to benzene mole ratio was 1.0; 0.5; and 0.25. The test was conducted by passing the feed over a MCM-22 catalyst at a temperature of 130° C. and at a pressure sufficient to maintain the benzene in the liquid phase. Results of the tests are shown in FIG. 6 through FIG. 8. FIG. 6, which plots the degree of 2-methylhexane isomerization to 3-methylhexane, shows the practice of the present disclosure results in minimal isomerization of 2-methylhexane to 3-methylhexane. FIG. 7, which plots the amount of n-propylbenzene impurity at various space velocities, shows that the amount of n-propylbenzene formation was not significantly changed by space velocity. FIG. 8, which plots cumene selectivity versus benzene conversion, shows that the practice of the present disclosure results in both high benzene conversion and high cumene selectivity.

What is claimed is:
1. A hydrocarbon composition, comprising:
  (i) benzene;
  (ii) from 1 to about 75 percent by weight based on the weight of the hydrocarbon composition, of at least one $C_6$+ non-aromatic hydrocarbon having a boiling point within 10° C. at a pressure of about 101.3 kPa-a of the boiling point of benzene;
  (iii) up to 5 wppm of sulfur;
  (iv) up to 1 wppm of nitrogen; and
  (v) up to 2500 wppm of olefins and dienes,
wherein said hydrocarbon composition is substantially free of $C_4$- hydrocarbons and $C_7$+ aromatic hydrocarbons.
2. The hydrocarbon composition recited in claim 1, wherein said at least one $C_6$+ non-aromatic hydrocarbon is present in said hydrocarbon composition in an amount from about 5 to about 60 percent by weight based on the weight of said hydrocarbon composition.
3. The hydrocarbon composition recited in claim 1, wherein said boiling point of said at least $C_6$+ non-aromatic hydrocarbons is within 5° C. at a pressure of about 101.3 kPa-a of the boiling point of benzene.
4. The hydrocarbon composition recited in claim 1, wherein said at least one $C_6$+ non-aromatic hydrocarbon is selected from the group consisting of cyclohexane, methylcyclopentane, 2-methylhexane, 3-methylhexane, 2,3-dimethylpentane, 2,4-dimethylpentane, dimethylcyclopentane, and mixtures thereof.
5. The hydrocarbon composition recited in claim 1, wherein said hydrocarbon composition is produced from a product formed by steam cracking of naphtha.
6. The hydrocarbon composition recited in claim 5, wherein said product formed by steam cracking of naphtha comprises:
  (i) $C_5$- hydrocarbons;
  (ii) benzene;
  (iii) $C_7$+ aromatic hydrocarbons;
  (iv) from about 1 to about 75 percent by weight of at least one $C_6$+ non-aromatic hydrocarbon having a boiling point within 10° C. at a pressure of about 101.3 kPa-a of the boiling point of benzene;
  (v) greater than 5 wppm of sulfur;
  (vi) greater than 1 wppm of nitrogen; and
  (vii) greater than 250 wppm of olefins and dienes.
7. The hydrocarbon composition recited in claim 6, wherein said hydrocarbon composition comprises a $C_6$ hydrocarbon fraction recovered from said product formed by steam cracking naphtha, said $C_6$ hydrocarbon fraction being recovered by the steps of:
  (a) removing $C_4$- hydrocarbons from said product;
  (b) removing sulfur and nitrogen from the product of step (a) to produce a resulting product containing up to 5 wppm of sulfur and up to 1 wppm of nitrogen;
  (c) fractionating in a distillation zone the resulting product of step (b) to form a $C_5$- fraction and a $C_6$+ fraction:
  (d) withdrawing said $C_6$+ fraction from said distillation zone;
  (e) treating said $C_6$+ fraction to remove olefins and dienes from said $C_6$+ fraction to form a resulting $C_6$+ fraction containing up to 250 wppm of olefins and dienes;
  (f) fractionating in a distillation zone the resulting $C_6$+ fraction of step (e) to form a $C_6$ fraction and a $C_7$+ fraction; and
  (g) withdrawing said $C_6$ fraction.
8. The hydrocarbon composition of claim 1, wherein said hydrocarbon composition is recovered from a reformate by a recovery process free of extracting step.

* * * * *